United States Patent [19]
Marshall

[11] Patent Number: 6,090,051
[45] Date of Patent: Jul. 18, 2000

[54] METHOD AND APPARATUS FOR EYE TRACKING AND MONITORING PUPIL DILATION TO EVALUATE COGNITIVE ACTIVITY

[76] Inventor: Sandra P. Marshall, 6475 Alvarado Rd., Ste. 132, San Diego, Calif. 92120-5013

[21] Appl. No.: 09/261,641

[22] Filed: Mar. 3, 1999

[51] Int. Cl.[7] ..................................................... A61B 3/00
[52] U.S. Cl. .......................................... 600/558; 351/210
[58] Field of Search .................................. 351/202, 205, 351/210, 223, 224, 221, 206; 600/558; 128/898

[56] References Cited

U.S. PATENT DOCUMENTS 5,617,872  4/1997  Scinto et al. ............................. 600/558
5,632,282  5/1997  Hay et al. ................................. 600/558

*Primary Examiner*—George Manuel
*Attorney, Agent, or Firm*—James C. Weseman, Esq.; The Law Offices of James C. Weseman

[57] ABSTRACT

Method and apparatus for correlating pupillary response to the cognitive activity of a subject undergoing an evaluation of cognitive activity during a task which involves monitoring and recording the point of gaze and pupillary response of the subject to the task, subjecting the recorded pupillary response to wavelet analysis in order to identify any dilation reflex of the subject's pupil during the task, and assigning a pupillary response value to the result of the wavelet analysis.

16 Claims, 4 Drawing Sheets

Scale:
100=4mm
1 obs= 17 msec

METHOD AND APPARATUS FOR EYE TRACKING AND MONITORING PUPIL DILATION TO EVALUATE COGNITIVE ACTIVITY

STATEMENT OF GOVERNMENT RIGHTS

The present invention was made in part under Grant No. N00014-93-1-0525 from the Office of Naval Research and Grant No. F49620-97-1-0353 from the Air Force Office of Scientific Research. Accordingly, the government may have certain rights in the invention.

TECHNICAL FIELD

The present invention relates to the evaluation of cognitive activity and, more particularly, to the monitoring and evaluation of point of gaze and pupil dilation as a correlate of such activity.

BACKGROUND OF THE INVENTION

Many complex tasks, including those in military command and control settings, now involve the use of visual displays, such as computer displays. Individuals using these displays are required to make efficient searches of their screens to locate pertinent information, and the speed and accuracy with which they do so impacts their ability to carry out their responsibilities. To evaluate an individual's performance as well as a display's usefulness, it is considered desirable to know precisely where and for long an individual looks at the display during critical times. In addition, in assessing the effectiveness of any visual display, it is useful to know not only what features of the display an individual focuses on, but whether cognitive activity occurs.

It has been proposed that pupillary response is a physiological correlate of cognitive activity, in that the pupil dilates as the subject gazes at a point which stimulates cognition. This relationship is part of the underlying rationale of Kahneman's theory of attention (Kahneman, D., *Attention and Effort*, Prentice-Hall, Englewood Cliff, N.J. (1973)) and has been the focus of a number of studies involving different cognitive activities including: Mental arithmetic (Hess, E. H. and J. M. Polt, *Science* 140:1190–1192 (1964); Bradshaw, J. L., *Quart. J. Expl. Psych.* 20:116–122 (1968); Ahern, S. and J. Beatty, *Science* 205:1289–1292 (1979)), sentence processing (Metalis, S. A. et al., *J. Applied Psych.* 65:359–363 (1980); Schluroff, M., *Brain and Language* 17:133–145 (1982); Just, M. A. and P. A. Carpenter, *Can. J. Expl. Psych.* 47:310–339 (1993)), visual search (Backs, R. W. and L. C. Walrath, *Appl. Ergonom.* 23:243–254 (1992)), and digit span recall (Gardner, R. M., et al., *Percep. Motor Skills* 41:951–955 (1975); Granhohn, E. et al., *Psychophysiol.* 33:457–461 (1996).

Pupil dilation is primarily the result of the integrated activity of two groups of muscles located in the iris. One set of muscles (the circular muscles) encircles the pupil; when activated, this set serves to constrict the diameter of the pupil and make it smaller. The second set of muscles (the radial muscles) lies immediately outside the circular muscles and extends radially from the pupil out through the iris. When activated, the radial muscles pull the pupil diameter outward and cause it to become larger. These two sets of muscles (the radial and the circular) typically work together through reciprocal innervation, a physiological process involving both agonistic and antagonistic responses.

In the presence of steady light, an individual's pupil responds with a continual but irregular oscillation. This movement is known as the light reflex, and it has been extensively studied. During the light reflex, the circular muscles act as the agonist and are stimulated to contract, while the radial muscles act as the antagonist and are inhibited from dilating the pupil. The reflex is fleeting, and the result is a visible pulsing of the pupil. This movement does not appear to be tied to other physiological systems such as respiration or heart rate (Lowenfeld, I. E., *The pupil: Anatomy, physiology, and clinical applications* (Volume I) Iowa State University Press, Ames, Iowa and Wayne State University Press, Detroit, Mich. (1993)).

When the individual experiences a psychosensory stimulus, e.g. a task requiring significant cognitive processing, the pupil may make a response that is quite different from the light reflex as the process of reciprocal innervation is reversed: The radial muscles are activated (causing the pupil to dilate), and the circular muscles are inhibited (also causing the pupil to dilate). The result is a brief dilation that is greater than either muscle group alone could effect. For this reason, the phenomenon is called the dilation reflex (Loewenfeld, 1993). Like the light reflex, the dilation reflex is a transitory event. In both instances, one observes a pulsing of the diameter, but with the dilation reflex the pulses are irregular and sharp, often exhibiting large jumps followed by rapid declines.

The fundamental problem in studying the relationship between cognitive activity and pupillary response lies in how to separate the dilation reflex from the light reflex. It is the dilation reflex that is important to measure, because this is the manifestation of cognitive workload (Loewenfeld, 1993). The dilemma is that both phenomena (dilation reflex and light reflex) may occur at the same time. Indeed, most cognitive tasks are carried out in lighted situations, which means that the light reflex will be present. Thus, it is considered desirable to develop a technique that can identify and remove the light reflex (essentially background noise) to reveal the dilation reflex that accompanies cognitive activity.

Two recurring themes have emerged from the cognitively-oriented research on pupil dilation: The pupil dilates as a result of effortful cognitive processing, and the degree of dilation varies with the degree of difficulty of the task. However, heretofore it has not been possible to look across tasks and compare the level or pattern of observed dilation because there is as yet no standard approach to measuring pupil dilation. Some researchers have adopted an averaging procedure; others have implemented a simple difference between adjacent observations; and others have used smoothing techniques from signal processing. Baseline measures differ from study to study, and virtually all reported data have been subjected to substantial and not always well-specified "preprocessing" of the data in order to produce meaningful representations. In short, researchers in this area have no unifying basis for comparisons either across tasks or across individuals as they attempt to understand the relationship between pupil dilation and cognitive processing.

DISCLOSURE OF THE INVENTION

The present invention involves the correlation of the pupillary response of a subject to a task during an evaluation of cognitive activity by identifying the occurrence of a pupil dilation reflex in the subject in response to the task.

In one aspect, the invention provides a method for correlating pupillary response to the cognitive activity of a subject. The method comprises monitoring the pupillary response of the subject undergoing an evaluation of cognitive activity which includes at least one task, recording the pupillary response of the subject to the task, subjecting the recorded pupillary response to wavelet analysis in order to identify any dilation reflex of the subject's pupil during the task, and assigning a pupillary response value to the result of the wavelet analysis.

In another aspect, the invention provides an apparatus for correlating pupillary response to the cognitive activity of a subject. In this aspect, the invention comprises a monitoring means for determining the pupillary response of a subject undergoing an evaluation of cognitive activity which includes at least one task, a recording means for recording the pupillary response of the subject to the task, and an analysis means for subjecting the recorded pupillary response to wavelet analysis in order to identify any dilation reflex of the subject's pupil during the task.

Optionally, the method and apparatus aspects of the present invention can each include the correlation of the pupillary response and the point of gaze of the subject during the task.

BRIEF DESCRIPTION OF THE DRAWINGS

FIG. 1 graphically depicts three different test conditions for one subject, in which FIG. 1A depicts the ordinary pupillary light reflex under typical experimental lighting, FIG. 1B depicts the pupil signal for the same subject when the room was darkened and the monitor turned off, and FIG. 1C depicts the pupil signal in the darkened room and dark screen condition when the subject engaged in active cognitive processing;

FIG. 3 graphically depicts three different test conditions for a second subject, in which FIG. 3A depicts the ordinary pupillary light reflex under typical experimental lighting, FIG. 3B depicts the pupil signal for the same subject when the subject was solving items on a spatial ability test, and FIG. 3C depicts the pupil signal in the darkened room and dark screen condition when the subject engaged in active cognitive processing.

DETAILED DESCRIPTION OF THE INVENTION

Figure 1:
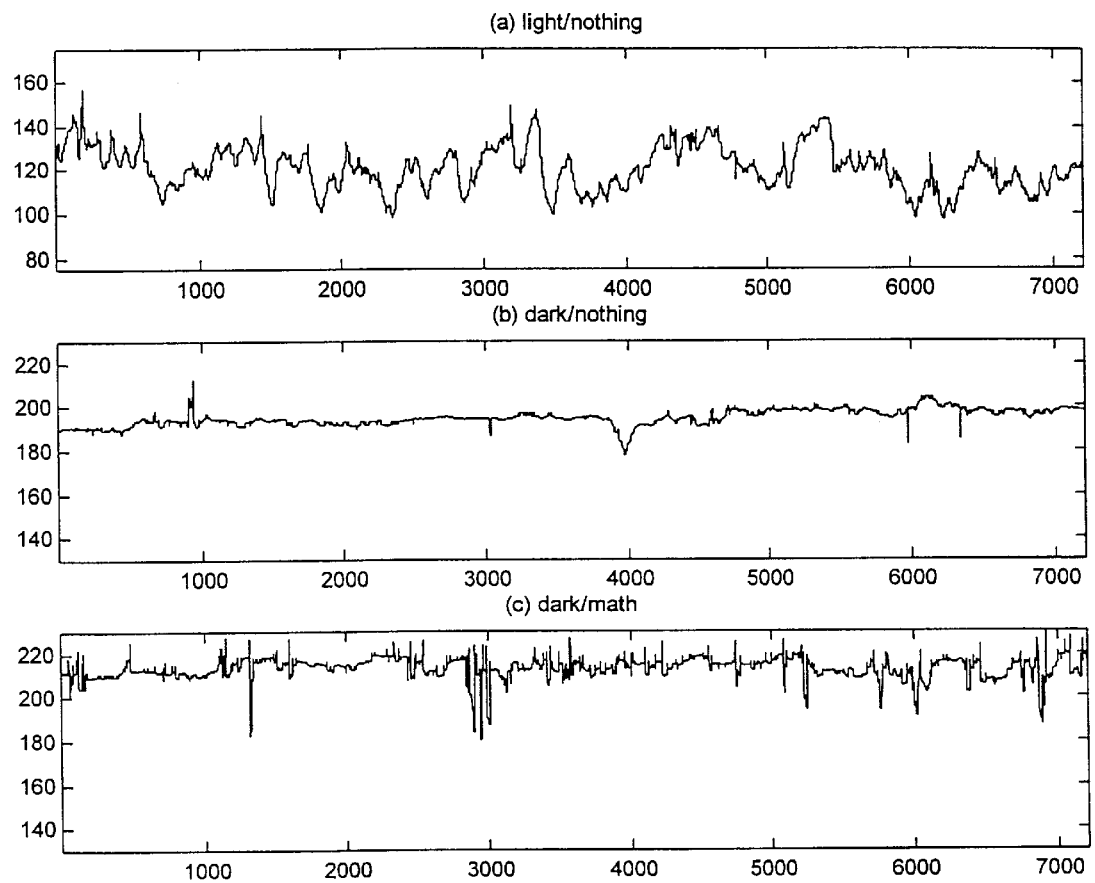

The present invention involves the correlation of the pupillary response of a subject to a task during an evaluation of cognitive activity by identifying the occurrence of a pupil dilation reflex in the subject in response to the task.

In one aspect, the invention provides a method for correlating pupillary response to the cognitive activity of a subject. The method comprises monitoring the pupillary response of the subject undergoing an evaluation of cognitive activity which includes at least one task, recording the pupillary response of the subject to the task, subjecting the recorded pupillary response to wavelet analysis in order to identify any dilation reflex of the subject's pupil during the task, and assigning a pupillary response value to the result of the wavelet analysis.

In another aspect, the invention provides an apparatus for correlating pupillary response to the cognitive activity of a subject. In this aspect, the invention comprises a monitoring means for determining the pupillary response of a subject undergoing an evaluation of cognitive activity which includes at least one task, a recording means for recording the pupillary response of the subject to the task, and an analysis means for subjecting the recorded pupillary response to wavelet analysis in order to identify any dilation reflex of the subject's pupil during the task.

Optionally, the method and apparatus aspects of the present invention can each include the correlation of the pupillary response and the point of gaze of the subject during the task.

As used herein, the term "task" may consist of a point of reference on a visual display, a unit of visual information which is intended to invoke some response in a subject viewing the display, any visual indicator which is intended to attract the attention of the subject, or any event intended to invoke cognitive activity.

As used herein, the term "point of gaze" is intended to mean the point of reference on a visual display upon which a subject's eye focuses for a measurable period of time.

As used herein, the term "pupillary response" is intended to mean any change in pupillary diameter which occurs in a subject's eye.

Eye Tracking Apparatus and System

Recent developments in eye tracking technology facilitate the evaluation of cognitive activity. Instruments to record eye movements have been available for at least 20 years, but have had limited used in evaluations of cognitive activity because the instruments were often too intrusive and uncomfortable for subjects to use, in part because they required rigid head restraints. Current technology involves lightweight head-mounted optics or remote optics systems that are non-invasive. Consequently, it is now possible to conduct studies in which subjects are not bothered by the apparatus and can concentrate instead on the task at hand.

Most eye-tracking studies documented in the literature involve tracking subjects' eyes for a brief duration, typically ranging from a few seconds to a few minutes (e.g., Beatty, J., *Psychological Bull.* 91:276–292 (1982); Just, M. A. and P. A. Carpenter, *Can. J. Expl. Psych.* 47:310–339 (1993); Backs, R. W. and L. C. Walrath, *Appl. Ergonomics* 23:243–254 (1992)). Some have extended the eye-tracking time to 10 minutes, especially in the study of aircraft pilots (e.g., Tole, J. R. et al., *Aviation, Space, and Environmental Medicine,* 53:54–59 (1982). However, the nature of many tasks require tracking for extended periods of time, ranging from 20 to 40 minutes.

Numerous eye tracking systems have been used in embodiments of the present invention. Two such systems, both manufactured by Applied Science Laboratories (ASL; Bedford, Mass.), are essentially identical for most purposes, although they have different model numbers (CU4000 and SU4000). Each system consists of a control unit, several small monitors for viewing the eye and/or the visual display and the head-mounted optics. The apparatus placed on a subject's head is a headband similar to the internal support found inside a football or bicycle helmet. A small camera with a near infrared illuminator is mounted on the headband above the subject's eye, and a monocle (which is roughly 3"×2") is positioned to lie below the subject's eye. The output of this device will be routed to the data recording system, typically a VCR. Also attached to the headband is a small sensor from a magnetic head tracking unit.

An additional system, the EyeLink System (SensoriMotorics Instrumentation (SMI), Germany), also has a headband on which cameras are mounted. Two cameras are positioned below the eyes so that the response for both the left and right eye are recorded. A third camera is located on the headband at approximately the middle of the forehead. This camera responds to infrared sensors placed on the monitor and records head movement. The cameras sample at 250 Hz. This system is presently preferred, as no additional magnetic head tracking system is required.

The system calibration is similar in the ASL and SMI systems. Each requires that the subject remain still and to look at a sequence of points on the screen. For each, the focusing of the camera(s) on the eye(s) is critical and takes some skill on the part of the operator. Each system produces point-of-gaze information in terms of screen coordinates and both yield estimates of pupil size.

In addition, each system requires several other components for satisfactory data collection; these include: A magnetic head-tracking system (for the ASL systems), a digital computer (typically with a pentium-class processor), a high quality scan converter, and a VCR for recording video data. A typical magnetic head tracker itself has multiple parts: The magnetic transmitter, which together with a gimbaled, pointing device is fixed to a support placed just behind the subject during the experiment; and a small sensor, which is placed on the headband during data collection. The output of the head-tracking system will typically be routed to the data recording system for subsequent processing.

It will be readily recognized that many alternative methodologies for eye tracking and measurement of pupillary diameter are available, and will be adaptable to the method of the present invention.

Data Collection

The proper set up of the eye tracking apparatus is important to obtain reliable data. Of great importance in the ASL system is the placement of the magnetic head tracker and the positioning of the subject's visual display with respect to it. Precise calibration of a subject's gaze depends upon the distance of the subject's head from the display screen, as well as the distance from the transmitter to the screen. These measurements are parameters used by the ASL software to configure the data.

When a subject has been seated before the display screen, the calibration of his eye with respect to the screen can be made. The headset is placed on his head and adjusted so that it fits snugly but without pressure. It has been found that this adjustment is best left under the control of the subject; the headset will be placed and the subject will be allowed to adjust the knobs that tighten it. If earphones are used, they are then placed over the eye tracking headset. And, finally, the camera is adjusted and focused so that the image of the pupil is reflected clearly on the ASL control unit.

To calibrate the system, the subject is asked to focus on a number of points on the display screen. This is the only time that the subject is asked to hold his head absolutely still; at all other times, he is free to move as he chooses. The calibration process is relatively brief; the subject is asked to look at each point in succession and a signal is passed to the control unit when he does so.

To record eye data from a subject, the camera transmits its signal to the control unit at a typical sampling rate (60 Hz or 250 Hz). First, the eye is illuminated by the near infrared beam on the headband, then the eye image is reflected in the monocle, and the camera transmits the resulting image. At the same time, the magnetic head tracker sends coordinate information about head location to the digital computer, and these signals are then integrated to provide point of gaze information using ASL software. Simultaneously, the VGA signal passes from the subject's display to the scan converter which outputs it as NTSC video to the control unit. The control unit superimposes a cursor indicating the point of gaze on the visual display and outputs the combination via video signal to the VCR. This configuration allows real time video recording of the display as the subject views it together with the point of gaze. The control unit also transmits the data in a binary stream to the computer for recording and subsequent data analysis.

In the ASL system, the signal from the magnetic head tracking system is integrated with the camera's pupil data to produce screen coordinates that capture the subject's point of gaze. Thus, the two measures of use are pupil diameter and point-of-gaze coordinates; both are recorded 60 times per second (60 Hz).

The visual display is generally divided into several regions of interest. These regions typically contain different information about a task or a plurality of tasks. The point-of-gaze data from the eye tracking system indicates precisely where the subject looked and for how long. Thus, as the subject views a region of the display, one can follow the fixations that occurred as each region is processed. And, as the subject scans the display, the regions which evoked a cognitive response can be identified.

A standard procedure with eye-tracking data is to calculate the fixations, generally defined as any gaze that remains fixed in a 1 degree by 1 degree region for more than 100 sec. A sampling rate of 60 Hz means that an observation is recorded every 16.7 msec. Thus, at least 6 observations with identical screen coordinates will be recorded before they are considered to be a fixation. With typical displays and typical subjects, fixations ordinarily last for 100–600 msec. In the practice of the present invention, both fixations and individual observations (i.e., not aggregating them into fixations) will find use as units of analysis Preprocessing of the Data Studies of pupillary response are faced with the problem of how to remove blink artifacts. A blink generally lasts about 70–100 msec (producing an artifact spanning 4–6 observations under 60 Hz sampling) during which time the camera registers loss and a pupil diameter of zero is recorded. Thus, it is generally relatively straightforward to detect and eliminate these contiguous zero observation artifacts from the record. However, on either side of a blink, one may also observe highly unusual recordings because the pupil may be measured inaccurately as the eye lid partially obscures the pupil. The result may be an impossibly small value for the pupil's size.

To insure that the analysis is conducted on pupil dilation and not on misleading discontinuities caused by blinks or partial blinks, one must either remove the blink observations from the data entirely or replace them with linearly interpolated values. Blinks (i.e., zero recordings) have been found to account for approximately 3–4% of all observations. Partial blinks account for another 1% of the total number of observations.

The blink-removal procedure removes all observations having zero values (i.e., the blink) as well as any extreme values that occur within six additional observations on either side of the zero value (i.e., partial blinks). The routine is conservative, removing any observation that differs by more than 0.1 mm from the two preceding observations.

The interpolation procedure identifies sets of blink and partial blink observations in the same manner as the blink-removal procedure. A linear interpolation is made for each set, using the observation that immediately precedes the set as the starting point of the interpolation and using the observation that immediately follows the set as the end point. The result is a signal of precisely the same length as the original pupil signal with the blinks and partial blinks replaced with values that fall at equal intervals between the start and end points.

Additional preprocessing of the data is occasionally found to be necessary, due to the possibility of electromagnetic interference (EMI). Depending upon the data collection environment, EMI could cause degradation of the data records. The possible sources of EMI should be identified and eliminated. When this does not prove feasible, the EMI can be eliminated from the data through digital signal processing, as described in greater detail below. Generally, however, EMI results in observations containing a impossible values, which are identified and treated in a manner similar to blinks.

Wavelet Analysis

The procedure utilized in the present invention for identifying the dilation reflex is derived from wavelet analysis, using relatively recent developments in applied mathematics (Daubechies, I., *Comm. Pure Appl. Math.* 41:909–996 (1988); Daubechies, I. *Ten lectures on wavelets,* SIAM, Philadelphia, Pa. (1992); Ogden, R. T. and E. Parzen, *Comp. Stat. Data Anal.,* 22:53–70 (1996); Donoho, D. L. and I. M. Johnstone, *Biometrika* 81:425–55 (1994)). Although aspects of wavelet analysis have been known for many years, it is only through the specification of a new set of wavelets and the resulting theoretical expansion that the technique has been widely applied to problems of signal decomposition and compression.

In general, wavelet analysis consists of repeated orthogonal transformations of a signal. The objective is to decompose the original signal into several independent components, each of which can be analyzed and interpreted. The basis for the wavelet analysis is a "mother wavelet," a small function that is both oscillatory and that decays rapidly to zero in both positive and negative direction, i.e., a little wave. For a given signal $\chi$ and a mother wavelet $\psi$, the process of wavelet analysis is expressed by the formula:

$$\psi_{jk}(\chi)=2^{j/2}\psi(2^j x-k)$$

where j is an index of dilation and k is an index of translation. The systematic variation of indices j and k will create a family of wavelets able to fully reproduce the original signal.

The choice of the "mother wavelet" is important, and it is desirable to select one that satisfies several important mathematical constraints. Only recently have mathematicians discovered the existence of families of wavelets that meet all or most of the desired constraints. In particular, Daubechies (1988, 1992) introduced a family of wavelets that is an orthonormal basis and that has compact support. Many orthogonal wavelet transforms are now known, and new ones appear frequently in the research literature. For example, several variants of Daubechies will be found to be useful, including Symlet Wavelets, Coiflet Wavelets, and Morlet Wavelets (Daubechies, 1992). Other families of wavelets are also effective, including the Battle-Lemarié family and the Chui-Wang family (Battle, G., *Comm. Math. Phys.* 100:601–615 (1987); Lemarié, P. G., *J. Mathematiques Pures et Appliquees* 67:227–236 (1988); Chui, C. K. and J. Z. Wang, *Proc. Am. Math. Soc.* 113:785–793 (1991)).

A number of products are now available commercially that make use of the, e.g. Daubechies wavelets, including the MATLAB Wavelet Toolbox by MathWorks, Inc., used in the preferred analyses of the present invention.

Wavelet analysis proceeds iteratively: Using the mother wavelet function, the dilation transformation first extracts high frequency details from the signal by setting index j=1 and evaluating all possible k. Next, using a scaling function that is orthogonal to the wavelet function, a second transformation extracts from the signal all information not captured by the wavelet transform. The initial wavelet transformation captures the largest abrupt changes or discontinuities in the signal. The scaling transformation results in a smoothing of the signal because these discontinuities have been removed.

The signal can be decomposed further if desired by repeatedly applying the wavelet transformation (i.e., j=2, 3, . . . for all k) and associated scaling function to the result of the most recent scaling transformation. Thus, additional details of the signal are extracted with subsequent wavelet transforms, and the signal becomes smoother with each ensuing application of the scaling transform. The result of the full analysis is a smoothed approximation of the signal (obtained from the final scaling transformation) together with multiple sets of detail coefficients. All parts of this decomposition are orthogonal, and the original signal will be obtained if the last approximation and all sets of details are summed.

The starting point in isolating the dilation reflex from the recorded data of pupillary response is the selection of an appropriate mother wavelet. With Daubechies wavelets, one selects the size of the original wavelet by taking into account the number of desired coefficients and the rate at which the data are sampled. For the 60 Hz ASL eye tracking system, the Daubechies(4) wavelet is satisfactory, and for the 250 Hz SMI eye tracking system, the Daubechies(16) is appropriate. Given the difference in sampling rates for the two systems (60 Hz versus 250 Hz), these two wavelets are essentially equivalent in their time span, i.e., the mother wavelet of Daubechies(4) has 8 coefficients and would cover 8×16.7= 134 msec (at 60 Hz), and the mother wavelet of Daubechies (16) has 32 coefficients and would cover 32×4=128 msec (at 250 Hz). Other wavelets that have been found to be useful include Daubechies(10) and Daubechies(7).

A key statistical question that arises in wavelet analysis of signals such as the pupil dilation signal is whether one can look at the signal at a specific point in time and determine if there was a significant change in the signal at that instant. Intuitively, one would expect that if there is a large change in the signal, a large coefficient in the detail component extracted from the signal will be observed. As always, the determinative issue is size. How large should the wavelet coefficient be to clearly indicate that it represents a significant change in the signal?

To answer this question, it is restated as: Could the values observed be simply the result of random noise in the data? The answer depends on how accurately the noise and the variability in the signal are estimated. Ogden (Ogden, R. T., *Essential wavelets for statistical applications and data analysis,* Birkhauser, Boston, Mass. (1997)) and Ogden & Parzen (1996) have shown that wavelets are well suited to solving statistical change-point problems when the objective is to determine whether the jumps observed in a signal are statistically significant. The underlying statistical model comes from nonparametric regression. Ogden and Parzen (1996) compared a number of different de-noising techniques, and their analyses suggest that several techniques are appropriate. All procedures operate by first establishing a threshold and then setting all wavelet coefficients that fall below the threshold to zero. The threshold is determined by framing the problem as one of multivariate normal estimation.

The de-noising technique employed in certain embodiments of the invention is based on the statistical principle of "minimax threshold estimation" developed by Donoho and Johnstone (1994). It is a standard option available in most programs for wavelet decomposition. With "minimax" estimation, noise is assumed to be Gaussian with standard deviation t, and the threshold estimator minimizes mean squared error. The wavelet coefficients extracted as details from the de-noised signal are the coefficients that exceed the threshold. These non-zero coefficients are interpreted in the present invention as indicating the precise time and intensity of cognitive activity. Thresholds can be set to be either "hard" or "soft," depending upon the quality of smoothing desired in the wavelet decomposition and "denoising." In general, soft thresholds give a more even look to the signal but contain smaller values than hard thresholds; both are appropriate. Other thresholds that may be used in this procedure include universal thresholding, which is a variant of the minimax threshold rule and Stein's Unbiased Risk Estimate (SURE) thresholding (Stein, C., *Ann. Stat.* 10:1135–1151 (1981); Donoho, D. L. and I. M. Johnstone, *J. Am. Stat. Assoc.* 90:1200–1224 (1995); Ogden, 1997).

Using Wavelets to Analyze the Pupil Signal

The experimental examples provided herein include measurements of two female subjects aged 25–30 years who are observed under several different experimental conditions over a period of several weeks. The data are collected using either ASL's E4000 Eye Tracking System in conjunction with Ascension's 'Flock of Birds' Magnetic Head Tracker (available as a package with the ASL system), or SMI's EyeLink System, generally in accordance with the instructions provided by the respective manufacturers.

The ASL eye-tracking apparatus consists of a head-mounted camera and optics unit attached to a headband. The camera unit is positioned above the subject's left eye, and a monocle is positioned just below the eye. Also attached to the headband is a small sensor from the magnetic head tracking unit. The camera records pupil diameter measurements at 60 Hz. The SMI apparatus utilizes two cameras positioned below the eyes so that the response for both the left and right eye are recorded. A third camera is located on the headband at approximately the middle of the forehead. This camera responds to infrared sensors placed on the monitor and records head movement. The cameras in the SMI system sample at 250 Hz.

For all conditions, subjects are tested under the same general conditions: They are seated approximately 18–20 inches in front of a 17 inch computer monitor in an experimental room with moderate indirect lighting. To begin each session, the subject underwent a calibration procedure to be sure the system was operating properly and that it was transmitting accurate information about direction of gaze and pupil size. The calibration procedure calls for the subject to gaze at a series of numbers on the computer screen. The brightness of the screen (and the background lighting of the room) are held constant by taking measurements with a Sony Spot Meter and adhering to a standard meter reading (EV) of 9.4 for all calibrations.

Procedures For Analyzing Cognitive Workload

Pupillary tracking equipment produces a great deal of data which requires substantial organization and reduction prior to proper interpretation. The steps utilized in the present invention include preprocessing the data, preparing the data, wavelet analysis and interpretation.

Preprocessing of the Data

Studies of pupillary response are faced with the problem of how to remove blink artifacts. A blink generally lasts about 70–100 msec (producing an artifact spanning 4–6 observations under 60 Hz sampling) during which time the camera registers loss and a pupil diameter of zero is recorded. Thus, it is generally relatively straightforward to detect and eliminate these contiguous zero observation artifacts from the record. However, on either side of a blink, one may also observe highly unusual recordings because the pupil may be measured inaccurately as the eye lid partially obscures the pupil. The result may be an impossibly small value for the pupil's size.

To insure that the analysis is conducted on pupil dilation and not misleading discontinuities caused by blinks or partial blinks, a blink-removal procedure can be applied to the data. The procedure eliminates all observations having zero values (i.e., the blink) as well as any extreme values that occur within six additional observations on either side of it (i.e., partial blinks). The routine is conservative, removing any observation that differs by more than 0.1 mm from the two preceding observations. Blinks (i.e., zero recordings) account for approximately 3–4% of all observations. Partial blinks account for another 1% of the total number of observations, resulting in a total data reduction of 4–5% for typical subjects. No additional preprocessing of the data is generally found to be necessary.

Preparing the data

The raw data file produced by the eyetracking apparatus is in binary form; it is converted to ascii using software supplied with each system, generally as follows:

for ASL data:
(1) in the subdirectory containing the program EDT2ASC.EXE, double click the icon for the program,
(2) when prompted, enter the name of the original data file with its .ehd extension,
(3) the converted file will have the same name as the original data file but will have .asc extension.

for SMI data:
(1) go to the DOS prompt at the subdirectory containing EDF2ASC.EXE
(2) to create the numerical data file for the left eye, at the prompt type:
EDF2ASC<original file.edf><new file.asc>−1−s −miss 0
(3) to create a file with the events and messages, run the program a second time:
EDF2ASC <original-file.edf><new_file.evt>−e
(4) for right eye data, repeat stems (2) and (3) using −r instead of −1. rename all .dat files to remove extension .dat
Example: S43.edf original_file
S43.dat new data file
S43.evt new event file
S43 renamed data file For both SMI and ASL data, measure the areas of interest (AOIs).

Before full analysis, the AOIs will have been identified and their coordinates entered into a MATLAB file. See the files as follows:
c:\matlab\bin\cogload_asl\aoi_cic2 (for ASL files)

c:matlab\bin\cogload_smi\aoi\dss2 (for SMI files) for examples of how the files should appear. All four dimensions (top, bottom, left, right) will have been set in inches for ASL or in pixels for SMI. Measure every region and determine the four dimensions for each one.

Data analysis

The data analysis generally has three major steps: Pre-processing the data to remove blinks and artifact observations (i.e., the occasional observations that result from partial blink or other intrusion); identifying the observations having cognitive workload; and, if desired, matching each observation with its specific location on the screen, using regions previously identified.

This analysis proceeds as follows:

(1) Open MATLAB program and go to the subdirectory cogload asl for ASL files or to the subdirectory cogload smi for SMI files.

(2) Open the script named "full_analysis"

(3) Type the full path name of the data file to be analyzed in the 21 line from the top of the file.

(4) Type X=file on the $3^{rd}$ line (e.g., X=tao107d_r).

(5) Type the subdirectory path in the $_3$rd line from the bottom to specify where the output is to be stored.

(6) Save the script (without renaming it) and close it.

(7) Open the file "id_dwells"

(8) On line 4, enter the name of the AOI file created above in step 2, replacing aoi-cic2 with selected file name:

[aoi_list]=aoi_cic2(hor,vert,orig_pd); save the file and close it.

(9) In MATLAB program, run the script full_analysis which contains all the necessary calls to functions that need to be made.

In the details below, functions are underlined and written in bold type.

(1) The first step is to preprocess the data using the function preprocess_data: The script will clean up the data using a number of special functions:

(a) First it loads the file and assigns key vectors using the function set_pdxy. The following variables are created:

pd=pupil diameter of current observation hor=horizontal coordinate of current observation vert=vertical coordinate of current observation dist=distance from eye to screen (only for ASL files)

XDAT=a timing signal sent from the display software to the eye tracker

The XDAT signal can indicate change of display screen, subject keyboard response, or subject mouse response. The use of this variable depends upon the particular material being tracked.

Each of these vectors will be of size (nxl) where n is the number of total observations in the file.

(b) Next the script removes any suspect observations from the data that could have been caused by electromagnetic interference (EMI) using the function emi. (NOTE: this only applies to ASL data). Two new variables are created:

Emi_pd inserts 0 into pd for all observations containing impossible values

Em_dist inserts 0 into dist for all observations containing impossible values

NOTE: If an observation i has bad data for either pd or dist, both pd(i) and dist(i) are replaced with 0.

(c) At this point, the function singleton is applied to replace unusual single values that occur in pd with 0's. These singletons typically are partial blinks. The variable pd now contains original values plus 0s for cases of EMI or singletons.

(d) In the original data, blinks are typically a series of 0's in pd that may be preceded or followed by several intermediate values that are too small to be legitimate readings. All of these can be removed by employing the function sim_blinks or asl_blinks (depending upon which eye tracker produced the data). These functions are applied iteratively, replacing values with 0s when blinks are found. Typically, seven iterations are used to reach a stable solution.

Occasionally, the removal of blinks from the data recording leaves a discontinuity between the last non-zero observation prior to the blink and the first nonzero observation following the blink. The function repair_pd checks to find the largest non-blink discrepancy elsewhere in the data and then compares the pre- and post-blink discrepancy to it. If the blink discrepancy is too large, observations adjacent to the blink are removed and a new discrepancy is calculated. The function continues to remove observations until a reasonable transition occurs. Typically, four iterations will suffice to accomplish this task.

(e) To prepare the data for MATLAB, all 0 observations are replaced with NaNs using the function fill_nan. The result is saved as the variable orig_pd, which has same length as original pd but has NaNs for unacceptable observations (f) Finally, the function excise removes the NaNs from orig_pd, creating a variable final_pd which contains only usable values (will be about 5% shorter than pd)

Next the script identifies cognitive workload using two approaches. The function id_cogload is used here.

Wavelet analysis

The first approach applies wavelet decomposition using one wavelet in the selected family. This approach calls several MATLAB Wavelet Toolbox functions via special utility functions such as big1_4, big1_10, and b1_16 for Daubechies(4), Daubechies(10), and Daubechies(16) wavelets. The Toolbox functions are dwtmode, wavedec, appcoef, detcoef, wrcoef, and wden.

First the original signal is decomposed using the wavelet decomposition function wavedec. (The function wavedec operates either on the data vector pd or on the blink-removed shortened form of it called final_pd.)

Following the wavelet decomposition, the signal is denoised using the MATLAB function wden, applying a minimax rule and hard threshold.

The denoised signal is then subjected to the same wavelet decomposition as applied to the original function. The resulting wavelet transformation contains the denoised detail. This variable is called x_dn.

After the final decomposition, the variable x_dn will be adjusted in length if the initial decomposition was made on the blink-removed (rather than the blink-interpolated) data. In this case, the function insert_NaN inserts placeholders into the x_dn vector at all locations that blinks occurred. The result is the vector final xdn which is the same length as the original pupil signal.

The invention utilizes comparable procedures for SMI and ASL. The differences are as follows: The scale of measurement for the pupil is very different for each system, so functions that operate on pupil size will be adjusted. A typical value for ASL is 100–150; a typical value for SMI is 2500–3000. The sampling rates, as noted above, are different, with 60 Hz for ASL and 250 Hz for SMI. Thus, the selected wavelets will be different (one is four times as large as the other). The underlying functions for identifying cognitive workload are identical. Only a few of the functions are different, but it is considered desirable to maintain two complete sets (one for each system) to insure that the desired ones are used on the data.

Statistical approach

The second approach looks for discontinuities in the original signal, calculating the moving average of the previous observations as well as their standard deviation. Deflections from the last observation to the current observation are examined in terms of the size of the deflection and whether it is unusual (e.g., 5% increase). A comparison is made on the basis of the standard deviation of the previous n observations, where n can be set by the user. The functions spikes_asl and spikes_smi are used here. One new variable e is created and is of the same size as final_pd:

e=1 for large positive jumps

−1 for large negative dips 0 otherwise

The variable e now should be lengthened with insert_nan so that it has the same size as the orig_pd vector and the denoised full_xdn vector. A new variable is created:

new_e the full sized vector e

Finally, the vectors new_e and full_xdn are examined together to find the observations at which new_e is positive and full_xdn is large. These observations are defined as those that contain cognitive workload. One new variable is created cogload a vector of the observation numbers of the cognitive load episodes Finally, the script checks each observation and determines the specific region in which it occurs. Ultimately, these will be mapped against the cogload observations so as to identify the regions in which cognitive load is found. The function id_dwells is called here.

The first step is to generate a new vector that contains the region (by number) in which the current observation is located. This variable is called aoi_list a vector of the same length as orig_pd, containing AOIs Next, the function count_aois is used to compute the frequency of each AOI as well as the total amount of time spent in it (determined by the number of observations that fall into each area). The new variables here are:

frequency the frequency distribution over defined regions plus 'off' duration total amount of time for each frequency bin

At this point, dwells (i.e., consecutive observations in the same region) are computed with the function make_dwells. New variables are:

dwells a vector of AOI numbers indicating the location of each dwell dwell_obs the number of observations found in the corresponding dwell The function cum_dwl_time now computes the duration in msec for each dwell and returns the variable cum_dwl the duration of each dwell Next, the probability transition matrix for moving from one AOI region to another is computed. The function transitions returns two variables:

p_trans the nxn transition matrix of probabilities, where n is the number of AOIs trans the nxn transition matrix of frequencies Finally, the function cog_dwell is used to compute three new variables that relate the location of the cognitive load to the dwell in which it occurs. These variables are:

cog_dwell a vector containing the AOI number for the episode of cognitive load

Msec the length in msec for each episode of cognitive load dwl_num the ordered number of the dwell in which the episode occurred The last step of full_analysis is to switch automatically to the subdirectory in which the data are to be stored and to save the entire set of variables for further analysis. At this point the following variables should be in the workspace:

home_dir hor st_blink pd cogload sub_dir vert end_blink orig_pd spike blink_obs x_dn The above will be created by the most minimum analysis to compute cognitive workload. In addition, several variables whose names depend on the data being analyzed will also be present. These are:

<raw data matrix>the raw data

<name >_hv a matrix of horizontal and vertical coordinates

<name>_buttons XDAT information about screen changes, mouse events, and the like In the case of data having electromagnetic interferences, the following will be present also:

emi_pd, emi dist

If blinks are completely removed rather than interpolated, the following will be present also:

full_pd, full_xdn

If the full analysis of areas of interest and dwells is required, the following will be present also:

dwells, cum_dwl, dwl_num, cog aoi aoi_list, frequency trans, p_trans

As noted previously, the id_dwell function of the procedure is not always included, as in certain modes of interpretation, the important issue is whether the cognitive load occurs during a particular part of the task and identification of the point-of-gaze is not necessary.

Interpretation

Having the results of the data analysis, the subjects responses to the task and/or the visual display can be utilized in a number of ways. For example, when correlated to fixations (point of gaze), the data can be used to determine the display regions which elicit the greatest and least amount of attention from new (naive) subjects, and the manner in which such patterns change with increased exposure (experienced subjects). In an informational display, the regions which have the greatest impact on decision making can also be identified. In each case, the results of the analysis can be used to refine the visual displays for enhanced impact on both naive and experienced subjects.

Alternatively, the subject may display very rapid eye movements and not fixations (i.e., the eyes keep moving and don't stay in one place); it remains desirable to identify the cognitive load. Clearly, with the dark room tasks, there is no point of gaze because the subject is looking at a blank screen.

Experimental

The following examples serve to illustrate certain preferred embodiments and aspects of the present invention and are not to be construed as limiting the scope thereof.

Example 1: Pupillary Light Reflex and Pupillary Reflex Dilation

To illustrate the difference between dilation reflex and light reflex, a first subject was evaluated by the eyetracking apparatus generally as described above.

FIG. 1 presents three different test conditions for this subject. FIG. 1A shows ordinary pupillary light reflex under typical experimental lighting. This signal was obtained by having the subject gaze at an illuminated computer monitor in a moderately lit room (spot meter reading of 9.4 at the center of the display). No stimuli are displayed; the subject looked at the monitor for 15 minutes. FIG. 1A shows the first two minutes of evaluation (7200 observations).

FIG. 1B contains the pupillary signal for the same subject when the room was darkened and the monitor turned off. The subject gazed at the blank screen for two minutes, and no stimuli are presented.

Finally, FIG. 1C depicts the pupil signal in the darkened room and dark screen condition when the subject engaged in active cognitive processing, solving a series of mental arithmetic problems of varying difficulty.

FIG. 1 illustrates both the light reflex and the dilation reflex. The signal in FIG. 1A is typical of those observed in most experimental evaluations. The data contains a great deal of irregular oscillation, and it exhibits both high and low frequency components. The signal in FIG. 1B presents far less oscillation. The difference in the two can be attributed to the absence of light and the reduction of the light reflex. It is well known that the pupil of an alert subject will show very little fluctuation under these conditions (Lowenfeld, 1993). In the absence of light, the pupil will maintain a relatively stable (and large) size. The signal in FIG. 1C shows the impact of a mental stimulus in the absence of the light reflex. The fluctuations observed here are the result of the dilation reflex triggered repeatedly by the cognitive activity required to make the mental computations.

Figure 2:
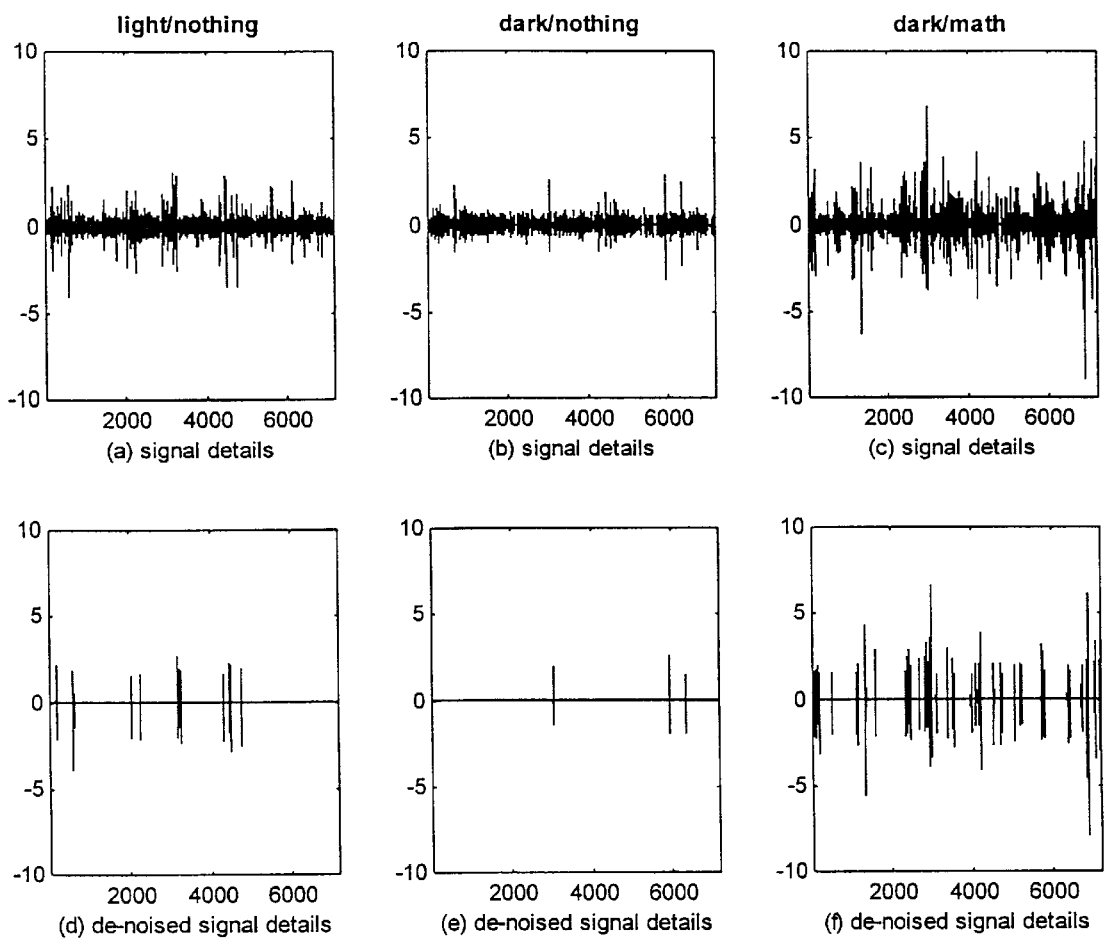
FIG. 2A–F graphically depicts the wavelet analysis of the data of FIG. 1.

Wavelet analysis. FIG. 2 displays the wavelet analysis of the data presented in FIG. 1. All wavelet analyses presented in FIG. 2 use Daubechies wavelet(10) and the minimax threshold for de-noising the signal, as described previously. The top row of FIG. 2 (A–C) shows the details extracted from the three signals presented in FIG. 1 (A–C). The bottom row (D–F) shows the details that are extracted after these signals are de-noised.

For the first two signals, most of the details extracted are not significantly different from noise. That is, they are essentially random values that could occur by chance. It is noted that these two signals are both obtained when the subject was not exerting effort to carry out cognitive processing. In contrast, the de-noised details from the third signal, obtained during the mental arithmetic task, contains a large number of significant coefficients.

Example 2: Cognitive Activity

Figure 3:
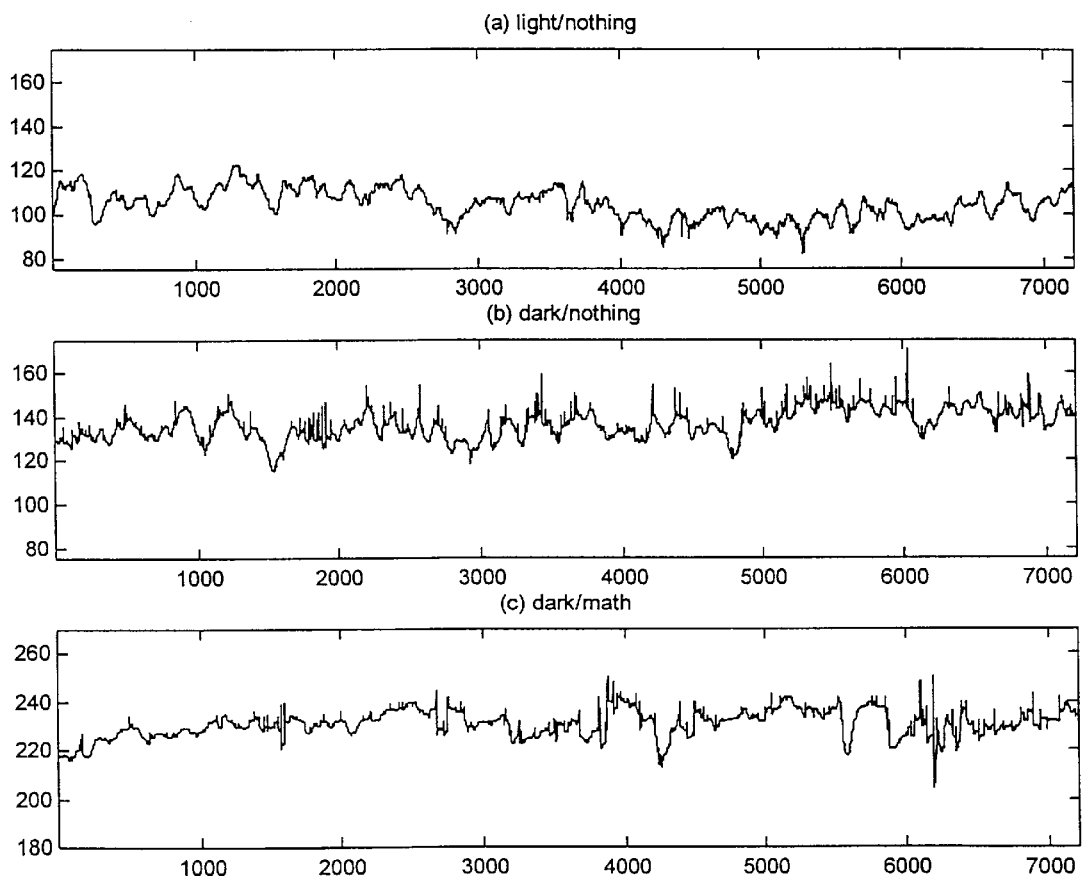

FIG. 3 shows measurements from a second subject who took part in two cognitive studies. The eye tracking apparatus was the same as in Example 1.

As in FIG. 1, panel 3A depicts the signal in a moderately lit room with an illuminated monitor (spot meter reading 9.4), with no presentation of stimuli. Panel 3B presents the pupillary signal obtained when the subject was solving items on the SANTRA, a spatial ability test that is comparable to Raven's Standard Progressive Matrices (Johnson, N. E. et al., Assessment 1:315–319 (1994)). In this task, items are presented one by one on the monitor and the subject used the mouse to make selections. Room and screen light are the same as for panel 3A. The two minutes of Panel 3B correspond to the time needed to respond to five tasks in the test. Panel 3C shows the pupillary signal obtained when the subject performed the same mental arithmetic task described for Example 1 (FIG. 1C) under dark room and dark monitor conditions.

Although all three signals in FIG. 3 show a great deal of oscillation, several important differences can be observed.

First, in the no-stimulus condition of FIG. 3A, there are no sharp upward deflections in the pupil diameter data. Instead, the increases are gradual from observation to observation. In contrast, there are a number of upward deflections observed in FIG. 3B and FIG. 3C. Moreover, when one looks at the reverse case, sudden decreases in pupil size, the results are reversed. There are a number of such instances in the no-stimulus condition depicted in FIG. 3A and very few in the problem-solving signals depicted in FIG. 3C. In both FIG. 3B and FIG. 3C, one observes increases with few decreases. The main difference between these two panels is the degree of general fluctuation, due to the reduction of light in the data of FIG. 3C.

Wavelet Analysis.

Figure 4:
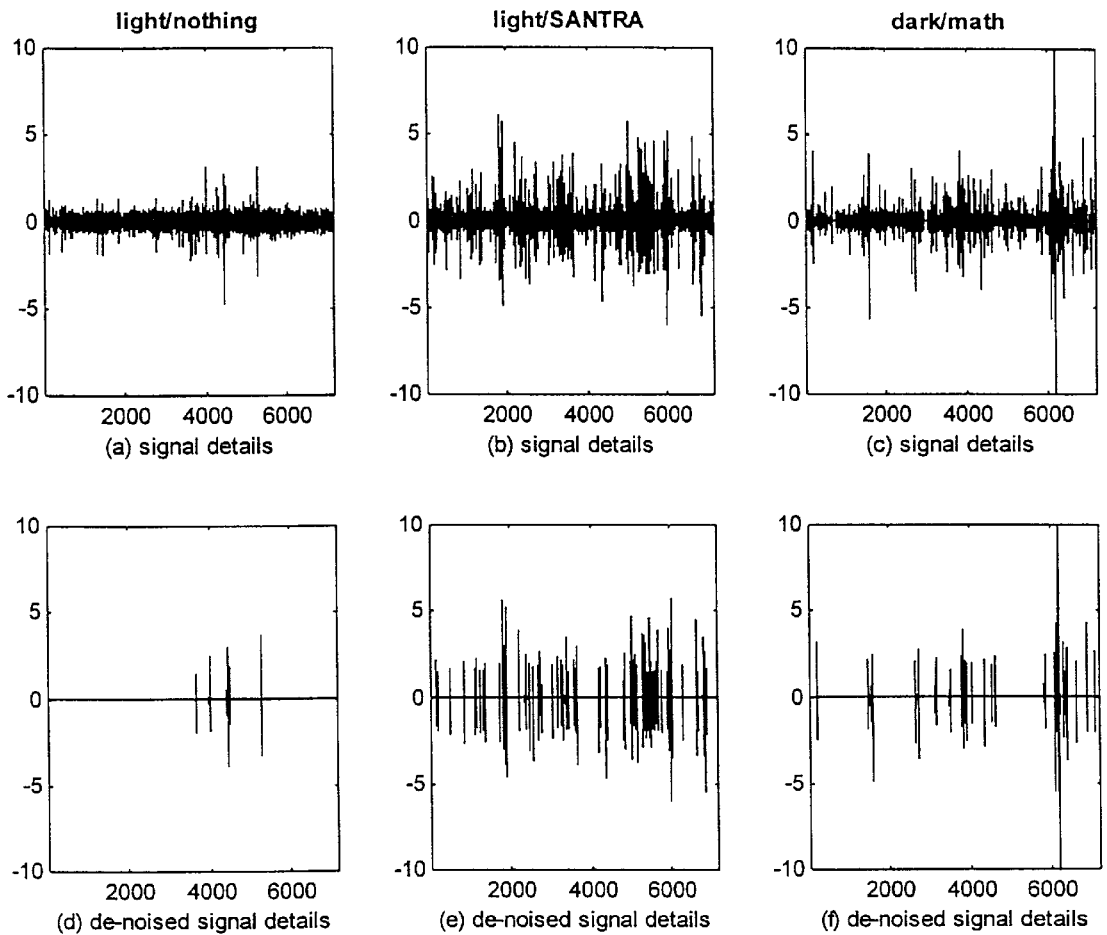
FIG. 4A–F graphically depicts the wavelet analysis of the data of FIG. 3.

FIG. 4 contains the results of wavelet analysis of the data presented in FIG. 3. Details from both the original signal and the de-noised signal are shown for the three signals. The results in the first column (FIG. 4A&D, i.e., Light/nothing) are similar to those for the first subject shown in FIG. 2A. Very few oscillations are observed that are not explained by random noise. The second (FIG. 4B&E) and third columns (FIG. 4C&F), however, show a number of significant coefficients after the signal has been de-noised.

One important advantage of wavelet analysis in the determination of cognitive activity from pupillary response is that it preserves information about the time and amplitude of the signal. Thus, one can examine the de-noised signal details to identify precisely when the large discontinuities occur. The observations in a signal are made either every 4 msec (with the SMI system) or every 16.7 msec (with the ASL system). Those observations accompanied by unexpectedly large pupil dilations emerge in the cognitive workload wavelet analysis.

Thus it is shown that by applying wavelet analysis to the recordings of point of gaze and pupillary diameter, an accurate correlation can be obtained with indicia of cognitive activity, providing a valuable tool to aid in the determination of mental responses to visual display stimuli. This correlation can be used to evaluate the effectiveness of the visual display or, conversely, the efficiency of the subject in responding to key information contained in the display.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

What is claimed is:

1. A method for correlating pupillary response to the cognitive activity of a subject comprising:
monitoring the pupillary response of a subject undergoing an evaluation of cognitive activity which includes at least one task;
recording the pupillary response of the subject to the task;
subjecting the recorded pupillary response to wavelet analysis in order to identify any dilation reflex of the subject's pupil during the task; and
assigning a pupillary response value to the result of the wavelet analysis as a measure of the cognitive activity.

2. A method as recited in claim 1 wherein said monitoring is conducted by sensing the pupillary diameter of said subject.

3. A method as recited in claim 1 wherein said analysis utilizes a digital processor.

4. A method as recited in claim 1 wherein said wavelet analysis is conducted by using the formula:

$$\psi_{jk}(\chi)=2^{j/2}\psi(2^j x-k)$$

to operate on signal $\chi$ and employing a mother wavelet $\psi$, where j is an index of dilation and k is an index of translation.

5. A method as recited in claim 4 wherein said wavelet analysis employs a mother wavelet $\psi$ selected from the group consisting of the Daubechies family of wavelets, Symlet wavelets, Coiflet wavelets, Morlet wavelets, the Battle-Lemarié family of wavelets, and the Chui-Wang family of wavelets.

6. A method as recited in claim 1 further comprising:

monitoring the point of gaze of the subject as a correlate to the pupillary response;

recording the pupillary response of the subject to the task when the point of gaze is fixed on the task;

subjecting the recorded pupillary response to wavelet analysis in order to identify any dilation reflex of the subject's pupil during fixation of the gaze on the task; and assigning a pupillary response value to the result of the wavelet analysis as a measure of the cognitive activity.

7. A method for correlating pupillary response to the cognitive activity of a subject comprising:

monitoring the point of gaze and pupillary response of a subject undergoing an evaluation of cognitive activity which includes at least one task;

recording the pupillary response of the subject to the task when the point of gaze is fixed on the task;

subjecting the recorded pupillary response to wavelet analysis in order to identify any dilation reflex of the subject's pupil during fixation of the gaze on the task; and assigning a pupillary response value to the result of the wavelet analysis as a measure of the cognitive activity.

8. A method as recited in claim 7 wherein said monitoring is conducted by sensing the pupillary diameter and viewing direction of said subject.

9. A method as recited in claim 7 wherein said analysis utilizes a digital processor.

10. A method as recited in claim 7 wherein said wavelet analysis is conducted by using the formula:

$$\psi_{jk}(\chi)=2^{j/2}\psi(2^j x-k)$$

to operate on signal $\chi$ and employing a mother wavelet tr, where j is an index of dilation and k is an index of translation.

11. A method as recited in claim 10 wherein said wavelet analysis employs a mother wavelet $\psi$ selected from the group consisting of the Daubechies family of wavelets, Symlet wavelets, Coiflet wavelets, Morlet wavelets, the Battle-Lemarié family of wavelets, and the Chui-Wang family of wavelets.

12. An apparatus for correlating pupillary response to the cognitive activity of a subject comprising:

monitoring means for determining the pupillary response of a subject undergoing an evaluation of cognitive activity which includes at least one task;

recording means for recording the pupillary response of the subject to the task; and analysis means for subjecting the recorded pupillary response to wavelet analysis in order to identify any dilation reflex of the subject's pupil.

13. An apparatus as recited in claim 12 further comprising monitoring means for determining the point of gaze of the subject; and recording means for recording the point of gaze correlated with the pupillary response of the subject to the task.

14. An apparatus as recited in claim 12 wherein said analysis means includes a digital processor.

15. An apparatus as recited in claim 12 wherein said wavelet analysis means employs the formula:

$$\psi_{jk}(\chi)=2^{j/2}\psi(2^j x-k)$$

to operate on signal $\chi$ and employing a mother wavelet $\psi$, where j is an index of dilation and k is an index of translation.

16. An apparatus as recited in claim 15 wherein said wavelet analysis means employs a mother wavelet $\psi$ selected from the group consisting of the Daubechies family of wavelets, Symlet wavelets, Coiflet wavelets, Morlet wavelets, the Battle-Lemarié family of wavelets, and the Chui-Wang family of wavelets.

* * * * *